US010301245B2

(12) United States Patent
Paul et al.

(10) Patent No.: US 10,301,245 B2
(45) Date of Patent: May 28, 2019

(54) USE OF MOLYBDENUM AND VANADIUM MIXED OXIDES AS CATALYSTS FOR THE OXIDATION OF UNSATURATED ALCOHOLS INTO UNSATURATED CARBOXYLIC ACIDS

(71) Applicants: CENTRE NATIONAL DE LA RECHERCHE SCIENTIFIQUE, Paris (FR); ECOLE CENTRALE DE LILLE, Villeneuve d'Ascq (FR); HOKKAIDO UNIVERSITY, Hokkaiddo (JP); UNIVERSITE DES SCIENCES ET TECHNOLOGIES DE LILLE-LILLE 1, Villeneuve d'Ascq (FR)

(72) Inventors: Sébastien Paul, Thun Saint Amand (FR); Benjamin Katryniok, Meurchin (FR); Franck Dumeignil, Villeneuve d'Ascq (FR); Marcia Araque Marin, Lille (FR); Toru Murayama, Hokkaido (JP); Wataru Ueda, Tokyo (JP)

(73) Assignees: Centre National de la Recherche Scientifique, Paris (FR); Universite des Sciences et Technologies de Lille 1, Villeneuve d'Ascq (FR); Hokkaido University, Hokkaido (JP); Ecole Centrale de Lille, Villeneuve d'Ascq (FR)

( * ) Notice: Subject to any disclaimer, the term of this patent is extended or adjusted under 35 U.S.C. 154(b) by 0 days.

(21) Appl. No.: 15/737,141

(22) PCT Filed: Jun. 18, 2015

(86) PCT No.: PCT/IB2015/001177
§ 371 (c)(1),
(2) Date: Dec. 15, 2017

(87) PCT Pub. No.: WO2016/203283
PCT Pub. Date: Dec. 22, 2016

(65) Prior Publication Data
US 2018/0215696 A1 Aug. 2, 2018

(51) Int. Cl.
*C07C 51/235* (2006.01)
*B01J 23/28* (2006.01)
*B01J 23/887* (2006.01)

(52) U.S. Cl.
CPC ............. *C07C 51/235* (2013.01); *B01J 23/28* (2013.01); *B01J 23/8877* (2013.01); *B01J 2523/00* (2013.01)

(58) Field of Classification Search
CPC ...... C07C 51/235; B01J 23/28; B01J 23/8877
See application file for complete search history.

(56) References Cited

FOREIGN PATENT DOCUMENTS

| JP | 2008-68217 A | 3/2008 |
|---|---|---|
| JP | 2008-162907 A | 7/2008 |

OTHER PUBLICATIONS

Guliants et al, Topics in Catalysis, Surface active sites present in the orthorhombic M1 phases: low energy ion scattering study of methanol and allyl alcohol chemisorption over Mo—V—Te—Nb—O and Mo—V—O catalysts, 2006, 38(1-3), pp. 41-50. (Year: 2006).*
Konya et al, Catalysis Science & Technology, An orthorhombic Mo3VOx catalyst most active for oxidative dehydrogenation of ethane among related complex metal oxides, 2013, 3, pp. 380-387 (Year: 2013).*
Kirk-Othmer, Encyclopedia of Chemical Technology, 4th Edition, 1993, vol. 5, pp. 383-389. (Year: 1993).*
Database Caplus [Online] Chemical Abstracts Service, Columbus, Ohio, US. Yoshida, Koichi et al.: "Preparation of Methacrolein and methacrylic acid from methallyl alcohol", JPN. Kokai Yokkyo Koho, 6 PP. Coden: 1998.
Kasuga, Hiroto et al.: "Preparation of allyl alcohol from glycerin using solid catalysts and preparation of acrylic acid from allyl alcohol by gas-phase catalytic oxidation", retrieved from STN Database Accession No. 2008:856978 abstract ; 2008.
Wladimir Suprun et al.: Catalytic activity of bi-functional transition metal oxide containing phosphated alumina catalysts in the dehydration of glycerol, Journal of Molecular Catalysis A: Chemical, Elsevier, Amsterdam, NL vol. 342 Apr. 29, 2011.
International Search Report dated Feb. 17, 2016.
Chen et al., "Single-Crystalline-Phase Mo3VOx: An Efficient Catalyst for the Partial Oxidation of Acrolein to Acrylic Acid," 2013, ChemCatChem Communications, pp. 2869-2873.
Office Action for JP Application 2017-565846 dated Mar. 26, 2019.

* cited by examiner

*Primary Examiner* — Paul A Zucker
(74) *Attorney, Agent, or Firm* — Thompson Coburn LLP; Steven M. Ritchey

(57) ABSTRACT

The present invention relates to the use of molybdenum and vanadium mixed oxides, optionally iron doped, as catalysts for the oxidation of unsaturated alcohols, in particular allyl alcohol, and also to a process for the production of unsaturated carboxylic acids, in particular acrylic acid, in the gas phase, in the presence of such a catalyst.

11 Claims, No Drawings

USE OF MOLYBDENUM AND VANADIUM MIXED OXIDES AS CATALYSTS FOR THE OXIDATION OF UNSATURATED ALCOHOLS INTO UNSATURATED CARBOXYLIC ACIDS

RELATED APPLICATION

This application is a National Phase of PCT/IB2015/001177, filed on Jun. 18, 2015 the entirety of which is incorporated by reference.

The present invention relates to the use of molybdenum and vanadium mixed oxides, optionally iron-doped, as catalysts for the oxidation of unsaturated alcohols, more particularly allyl alcohol, and also to a process for the production of unsaturated carboxylic acids, more particularly acrylic acid, in the gas phase, in the presence of such a catalyst.

Acrylic acid (or acroleic acid or prop-2-enoic acid) is an organic compound of global formula $C_3H_4O_2$ and of semi-structural formula $CH_2$=CHCOOH. Acrylic acid and its esters, namely acrylates, are widely used in the chemical industry, in particular for the preparation of superabsorbents, plastic materials, in acrylic paints and in various polyacrylic compounds that have multiple uses.

The industrial production of acrylic acid is today mainly dependent on propylene, which is a product issued from fossil resources, in particular from petroleum refining. Indeed, synthesis of acrylic acid is usually carried out by oxidation, in the gas phase at elevated temperatures (generally higher than 320° C.), of propylene in two or three steps, using acrolein as an intermediate product.

In particular, the main commercial process can be carried out in two steps starting from propylene to form acrolein as an intermediate product on a $BiMoO_x$ catalyst, and the acrolein is then oxidized to acrylic acid in a second step on a $MoVWO_x$ catalyst according to reactions (1) and (2) below:

$$CH_2=CH-CH_3+O_2 \rightarrow CH_2=CH-CHO+H_2O \quad (1)$$

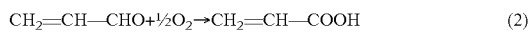

$$CH_2=CH-CHO+\tfrac{1}{2}O_2 \rightarrow CH_2=CH-COOH \quad (2)$$

As another example, U.S. Pat. No. 4,051,181 describes a three-step process for the production of acrolein and/or acrylic acid from propylene involving, in a first step, oxidizing the propylene in the presence of a palladium catalyst and acetic acid to produce allyl acetate, and, in a second step, in hydrolyzing the resulting allyl acetate to produce allyl alcohol and acetic acid, recycling the acetic acid produced to the propylene oxidation step, and finally, in a third step, in oxidizing the allyl alcohol in the presence of a supported palladium-copper or palladium-silver metal catalyst. However, this process exhibits the disadvantage of employing propene, the price of which being always increasing. It has also additional drawbacks since it involves three steps, the use of two different catalysts and does not lead to pure acrylic acid, but to a mixture comprising mainly acrolein (from 53% to about 72%) and only a weaker proportion of acrylic acid (from about 27% to 47%).

More recently, alternative processes for the production of acrylic acid which are independent of propylene have been proposed. As an example, Japanese patent application JP2008/162907 provides a process for the production of acrylic acid by oxidation of allyl alcohol, said alcohol being derived from glycerol. According to this process, glycerol is first dehydrated in the presence of an acidic catalyst to lead to a mixture of compounds comprising, among other compounds allyl alcohol, acrolein and 1-hydroxyacetone. These compounds need to be further distillated to recover an aqueous solution mainly comprising acrolein and allyl alcohol, this aqueous solution being then used in the oxidation reaction. The oxidation reaction is carried out in the gas phase in the presence of a complex molybdenum-based mixed oxide catalyst, namely $Mo_{12}V_4W_{2.5}Cu_2Zr_2O_x$. The best yield in acrylic acid obtained according to this process is about 70%. However, acid catalysts used for glycerol dehydration are generally unstable under reaction conditions (formation of coke) if, e.g., no $O_2$ or $H_2$ are injected in the feed during the reaction, which is the case according to the process disclosed in this patent. The performances of the process have been measured only after 3 hours under stream, which is not sufficient to notice the deactivation of the catalyst. In addition, this prior art process has the drawbacks of involving a costly distillation step and a complex process.

Finally, there are some research works to produce biopropylene from ethanol over zeolite catalysts, but the yields are still low and the cost of the as-obtained biopropylene is thus much higher than that of the petroleum-based one (Takahashi A; et al., Applied Catalysis A: General 423-424 (2012) 162-167).

A need thus still exists for a process for the preparation of acrylic acid or derivatives thereof, which is independent of propylene while resulting in better yields. The inventors set themselves in particular the aim of developing a process which makes it possible to produce in particular acrylic acid from allyl alcohol. Furthermore, the latter can be biosourced, which brings an environmental advantage to such a process. It was during these research studies that the inventors discovered that the use of a specific catalyst based on molybdenum and vanadium, said catalyst being optionally doped with iron, makes it possible in particular to catalyse, in a one-step process, the oxidation of allyl alcohol to acrylic acid, in the gas phase, with a very good yield.

A first subject-matter of the present invention is thus the use of a molybdenum and vanadium mixed oxide represented by the following formula (I):

$$Mo_aVFe_bO_c \quad (I)$$

wherein:
a, b, and c denotes the atomic ratio of Mo, Fe and O respectively;
a varies from 3 to 4 inclusive,
b varies from 0 to 1 inclusive,
c varies from about 10 to 15 inclusive,
said compound of formula (I) being in an orthorhombic or trigonal crystalline phase,
as a catalyst for catalysing the oxidation reaction of an alcohol of following formula (II) $CH_2=C(R^1)-CH_2-OH$ (II), in which $R^1$ represents a hydrogen atom or a methyl radical, to give a unsaturated carboxylic acid of following formula (III) $CH_2=C(R^1)-COOH$ (III), in which $R^1$ has the same meaning as in the above formula (II), said reaction being carried out in the gas phase, said gas phase comprising at least oxygen.

In the above formula (I), and in all compounds of formula (I) specifically mentioned in the rest of the present specification, it has to be noted that the value of c (when not indicated) is determined by the oxidized states of the other elements.

The use of the catalyst of formula (I) above makes it possible to carry out the oxidation reaction of an alcohol of formula (II) to result in an unsaturated carboxylic acid of formula (III), corresponding in particular to acrylic acid and methacrylic acid, in the gas phase, with a conversion of about 98 to 100% of the alcohol of formula (II) and a very good yield in the corresponding unsaturated carboxylic acid of formula (III), said yield being higher than 73% with orthorhombic $Mo_3VO_c$ and reaching about 80% with trigonal $Mo_3VFe_{0.2}O_c$. Furthermore, as mentioned above, the starting material (the alcohol of formula (II)) can be produced from renewable resources, which makes it possible to access the acids of formula (III) and in particular acrylic acid in total independence on fossil resources. For example, glycerol, alone or as a mixture with formic acid, can be used to produce allyl alcohol according to various catalytic processes in the gas phase or in the liquid phase described in the literature, in particular in International Applications WO 2008/092115 and WO 2011/08509.

Among the oxides of formula (I) above, compounds in which a=3, and b=0 to 0.5 inclusive are preferred. Among these oxides, trigonal $Mo_3VO_c$, orthorhombic $Mo_3VO_c$ and trigonal $Mo_3VFe_{0.2}O_c$, in which c has the same signification than in formula (I) above, are particularly preferred.

By way of example, the catalysts of formula (I) above can in particular be prepared by a hydrothermal method according to the process described by T. Konya, et al., *Catal. Sci. Technol.*, 2013, 3, 380-387.

Another subject-matter of the present invention is a process for the production of an unsaturated carboxylic acid from an unsaturated alcohol in the presence of a catalyst, said process comprising only one step of oxidation of an unsaturated alcohol of following formula (II):

$$CH_2=C(R^1)-CH_2-OH \qquad (II)$$

in which $R^1$ represents a hydrogen atom or a methyl radical, to result in an unsaturated carboxylic acid of following formula (III):

$$CH_2=C(R^1)-COOH \qquad (III)$$

in which $R^1$ has the same meaning as in the above formula (II), said reaction being carried out in the gas phase, the said gas phase comprising at least oxygen, and in the presence of a solid catalyst chosen from the compounds of following formula (I):

$$Mo_aVFe_bO_c \qquad (I)$$

wherein:
a, b and c denotes the atomic ratio of Mo, Fe and O respectively;
a varies from 3 to 4 inclusive,
b varies from 0 to 1 inclusive,
c varies from about 10 to 15 inclusive,
said compound of formula (I) being in an orthorhombic or trigonal crystalline phase.

The process in accordance with the invention makes it possible to proceed without fossil resources in the case where the starting materials (alcohols of formula (II) and in particular allyl alcohol) result from biomass. It is simple to carry out (just one stage) and very selective. It results in the unsaturated carboxylic acids of formula (III), in particular in acrylic acid ($R^1$=H), with yields of about 80% and a very good conversion of the alcohol of formula (II) which is about 98 to 100%.

When $R^1$ represents a hydrogen atom, then the alcohol of formula (II) is allyl alcohol and the unsaturated carboxylic acid of formula (III) is acrylic acid.

When $R^1$ represents a methyl radical, then the alcohol of formula (II) is methallyl alcohol and the unsaturated carboxylic acid of formula (III) is methacrylic acid.

According to a preferred embodiment of the invention, $R^1$ represents a hydrogen atom. Thus, according to this preferred embodiment, the process in accordance with the invention comprises a step of oxidation of allyl alcohol to give acrylic acid.

The solid catalyst is preferably chosen from the compounds of formula (I) in which a=3 and b=0 to 0.5 inclusive. Among these oxides, trigonal $Mo_3VO_c$, orthorhombic $Mo_3VO_c$ and trigonal $Mo_3VFe_{0.2}O_c$, in which c has the same meaning as in the formula (I), above are particularly preferred.

The oxidation reaction is preferably carried out at a temperature higher than or equal to approximately 300° C. and more preferably at a temperature varying inclusively from 330 to 370° C. approximately. A temperature of about 350° C. is even more particularly preferred according to the invention.

According to a preferred embodiment of the process in accordance with the invention, the oxidation reaction is carried out at a pressure ranging from 1 to $1 \cdot 10^6$ Pa and more preferably ranging from 1 to $3 \cdot 10^5$ Pa. A pressure of about $2 \cdot 10^5$ Pa is particularly preferred according to the invention.

The contact time, defined as being the ratio of the mass of catalyst (in g: g-cat) to the total flow rate of gas injected into the reactor (in mL·min$^{-1}$), calculated at 20° C. and at $10^5$ Pa, is preferably kept below 0.004 g-cat (mL·min$^{-1}$)$^{-1}$ approximately and more preferably below 0.002 g-cat (mL·min$^{-1}$)$^{-1}$ approximately.

Within the gas phase, the alcohol of formula (II)/oxygen molar ratio can vary from 0.1 to 2 approximately. According to a preferred embodiment of the invention, the oxidation reaction is carried out using a phase gas in which the alcohol of formula (II)/oxygen molar ratio is equal to 0.45 approximately.

According to a preferred embodiment of the present invention, the gas phase comprises a carrier gas. Such a carrier gas is for example helium and/or nitrogen.

According to a particularly preferred embodiment of the invention, the oxidation reaction is carried out using a gas phase comprising nitrogen as carrier gas and in which the alcohol of formula (II)/oxygen/nitrogen molar ratio is 1/2.2/11.8 approximately. In another particularly preferred embodiment of the invention, the oxidation reaction is carried out using a gas phase comprising a mixture of nitrogen and helium as carrier gas and in which the alcohol of formula (II)/oxygen/nitrogen+helium molar ratio is 0.7/1.5/8.

According to a specific embodiment of the process in accordance with the invention and although this is in no way necessary for the satisfactory progression of the oxidation reaction, the catalyst of formula (I) can be supported by a porous solid support. In this case, the porous solid support can be chosen from supports based on silica, in particular in the form of silica gel (CARiACT® type) or of mesostructured silica (such as, for example, the mesostructured silica of SBA-15 type), and also from supports based on mixed silicon oxides, such as, for example, $SiO_2$—$TiO_2$ or $SiO_2$—$ZrO_2$; and supports made of silicon carbide (SiC), and the like.

Such a porous solid support preferably exhibits a mean porosity of between 0.1 cm$^3$/g and 2.0 cm$^3$/g inclusive and more preferably still between 0.5 cm$^3$/g and 1.5 cm$^3$/g inclusive.

When the reaction is terminated, the separation of the coproducts of the reaction can be carried out by any appropriate technique known to a person skilled in the art, for example by distillation.

The present invention is illustrated by the following implementational examples, to which, however, it is not limited.

EXAMPLES

In the examples which follow, the following starting materials were used:
99% Allyl alcohol (Sigma Aldrich),
Oxygen (Air Liquide),
Helium (Air Liquide),
All these materials have been used as received from the suppliers, i.e., without additional purification.

The different catalysts used in the examples are listed hereafter:
Trigonal $Mo_3VO_c$, denoted Tr-MoVO,
Orthorhombic $Mo_3VO_c$, denoted Or—MoVO,
Tetragonal $Mo_3VO_c$, denoted Te—MoVO,
Amorphous $Mo_3VO_c$, denoted Am—MoVO,
Trigonal $Mo_3VFe_{0.2}O_c$, denoted Tr-MoVFeO,
Trigonal $Mo_3VCu_{0.14}O_c$, denoted Tr-MoVCuO,
Trigonal $Mo_3VNb_{0.13}O_c$, denoted Tr-MoVNbO,
Trigonal $Mo_3VTe_{0.23}O_c$, denoted Tr-MoVTeO,
Trigonal $Mo_3VTa_{0.38}O_x$, denoted Tr-MoVTaO,
Trigonal $Mo_3VW_{0.24}O_x$, denoted Tr-MoVWO,
Trigonal $Mo_3VW_{0.27}Cu_{0.14}O_x$, denoted Tr-MoVWCuO.

The above-mentioned catalysts were prepared as follows:

Preparation of Orthorhombic $Mo_3VO_c$ Mixed Oxide

As already mentioned, orthorhombic $Mo_3VO_c$ materials were synthesized by a hydrothermal method according to the process described by T. Konya, et al., *Catal. Sci. Technol.*, 2013, 3, 380-387.

$(NH_4)_6Mo_7O_{24} \cdot 4H_2O$ (Mo: 50 mmol, Wako) was dissolved in 120 mL of distilled water. Separately, an aqueous solution of $VOSO_4$ (Mitsuwa Chemicals) was prepared by dissolving 12.5 mmol of hydrated $VOSO_4$ in 120 mL distilled water. These two solutions were mixed at 20° C. and stirred for 10 min before being introduced into an autoclave (300 mL Teflon inner tube). After 10 min of nitrogen bubbling to replace the residual air, hydrothermal treatment was carried out at 175° C. for 48 hours. The as-obtained gray solids were washed with distilled water and dried at 80° C. overnight. These solids were purified by treatment with oxalic acid; dry solids were added to an aqueous solution of oxalic acid (0.4 M; 25 mL/1 g solid) and this mixture was stirred at 60° C. for 30 min. Solids were isolated from the suspension by filtration, washed with distilled water, and dried at 80° C. overnight.

Preparation of Trigonal $Mo_3VO_c$ Mixed Oxide

The same procedure as the one described for the synthesis of orthorhombic $Mo_3VO_c$ just above was used for the synthesis of trigonal $Mo_3VO_c$ except for pH condition and duration of hydrothermal synthesis. The pH value of the mixed solution was adjusted to 2.2 by adding sulphuric acid (2 mol $L^{-1}$). The hydrothermal synthesis time was 20 h.

Preparation of Amorphous $Mo_3VO_c$ Mixed Oxide $Mo_3VO_c$ material well-crystallized in the c-direction but disordered in the other direction was obtained by increasing the concentration of the mixed aqueous solution two-fold higher. Other preparatory conditions were the same as those described above for orthorhombic $Mo_3VO_c$.

Preparation of Tetragonal $Mo_3VO_c$ Mixed Oxide

Tetragonal $Mo_3VO_c$ was synthesized by phase transformation from orthorhombic $Mo_3VO_c$ by heat treatment. Dried orthorhombic $Mo_3VO_c$ was heated in air with a heating ramp of 10° C. $min^{-1}$ to 400° C. and kept at that temperature for 2 h before cooling to ambient temperature. The heat-treated sample was again heated in a nitrogen stream (50 mL $min^{-1}$) with a heating ramp of 10° C. $min^{-1}$ to 575° C. and kept at that temperature for 2 h.

Preparation of Trigonal MoVMO (M=Fe, Cu, Nb, Te, Ta, W, Cu and W)

1) Preparation of Ethylammonium Isopolymolybdate 22.594 g of $MoO_3$ (0.150 mol, Kanto) were dissolved in 40 wt. % ethylamine aqueous solution (ethylamine: 0.300 mol, Wako). After complete dissolution of the solid, the solution was evaporated under vacuum at about 70° C. and then a solid powder consisting of ethylammonium trimolybdate was obtained and dried in air at about 80° C. overnight.

2) Preparation of Trigonal MoVMO

Prepared ethylammonium trimolybdate (Mo: 50 mmol) was dissolved in 120 mL of distilled water. Separately, an aqueous solution of $VOSO_4$ (Mitsuwa Chemicals) was prepared by dissolving 12.5 mmol of hydrated $VOSO_4$ in 120 mL of distilled water. These two solutions and the additional precursor for M were mixed at about 20° C. and stirred for 10 min before being introduced into an autoclave (300 mL Teflon inner tube). The different precursors and their amount were as follows:

Tr-MoVFeO: $Fe(NH_4)(SO_4)_2 \cdot 12H_2O$ (0.63 mmol (Fe)),
Tr-MoVCuO: $Cu(NH_4)_2Cl_4 \cdot 2H_2O$ (0.13 mmol (Cu)),
Tr-MoVNbO: $Nb_2O_5 \cdot nH_2O$ (0.63 mmol (Nb)),
Tr-MoVTeO: $TeO_3 \cdot nH_2O$ (0.36 mmol (Te)),
Tr-MoVTaO: $Ta_2O_5 \cdot nH_2O$ (0.31 mmol (Ta)), and
Tr-MoVWCuO: $Cu(NH_4)_2Cl_4 \cdot 2H_2O$ (0.13 mmol (Cu)) and $(NH_4)_6[H_2W_{12}O_{40}] \cdot nH_2O$ (0.63 mmol (W)).

After 10 min of nitrogen bubbling to replace the residual air, hydrothermal reaction was carried out at about 175° C. for 48 h. Obtained gray solids were washed with distilled water and dried at about 80° C. overnight. These solids were purified by treatment with oxalic acid; dry solids were added to an aqueous solution of oxalic acid (0.4 M; 25 mL/1 g solids), and this mixture was stirred at about 60° C. for 30 min. Solids were isolated from the suspension by filtration, washed with distilled water, and dried at about 80° C. overnight.

These catalysts have been activated by calcination at 400° C. in static air during 2 hours before their use in the catalytic tests.

The synthesis of acrylic acid was carried out in the gas phase in a tubular fixed bed reactor with a inner diameter of 2.6 mm (outer diameter 3 mm) and a length of 300 mm. Injection of allyl alcohol has been performed with a high pressure liquid chromatography (HPLC) pump sold under the denomination PU-2080 by the firm Jasco. The temperature of the reactor was precisely regulated and controlled by a thermocouple.

Example 1

Synthesis of Acrylic Acid with Trigonal or Orthorhombic Molybdenum and Vanadium Mixed Oxides According to the Invention—Comparison with Catalysts not Forming Part of the Present Invention In this example, acrylic acid has been synthetised in gas phase (using nitrogen as carrier gas) starting from allyl alcohol, using trigonal $Mo_3VO_c$ (Tr-MoVO) or orthorhombic $Mo_3VO_c$ (Or—MoVO). Comparatively, the synthesis of acrylic acid has also been carried using catalysts not forming part of the present invention, namely tetragonal $Mo_3VO_c$ (Te—MoVO) and amorphous $Mo_3VO_c$ (Am—MoVO).

For each synthesis, 50 mg of catalyst have been placed between 2 layers of silicium carbide having a mean granulometry of 210 μm. The reactor was heated until the required temperature (300 or 350° C.) under an air flow of 10 mL/min and then fed with reactants (allyl alcohol/$O_2$/$H_2O$/$N_2$) at a pressure of $2·10^5$ Pa. The flow rate was adjusted to 40 mL/min. The contact time of the reactants with the catalyst was of the order of 0.00125 g-cat $(mL·min^{-1})^{-1}$ and the total reaction time was 140 min. The allyl alcohol/$O_2$/$H_2O$/$N_2$ molar ratio was set at 1/2.2/42.1/11.8 for all the experiments.

The liquid and gaseous products resulting from the reaction were analysed after trapping at the reactor outlet in a bubbler maintained at a temperature of about 10° C. The liquid obtained was subsequently analysed on a gas chromatograph equipped with a flame ionization detector.

The temperature conditions and corresponding results are summarized in Table I below:

(moles of allyl alcohol injected)−(moles of allyl alcohol analyzed at the outlet of the reactor)]×100.

These results show that the total conversion of allyl alcohol ranges from 34.8 to 100% for the different tested catalysts, and the acrylic acid selectivity varies from 0.9 to 66.3. The best conversion of allyl alcohol (66.3%) is obtained with Or—MoVO used at 350° C. The main coproducts of the reaction are propionic acid, acetic acid, acrolein and carbon oxides ($CO_x$). This demonstrates that the crystalline structure has a very important impact on catalytic properties of molybdenum and vanadium mixed oxides for the oxidation of allyl alcohol to acrylic acid. These results also demonstrate that a better selectivity in acrylic acid is observed when the oxidation reaction is carried out at a temperature of 350° C.

Example 2

Synthesis of Acrylic Acid with Optionally Iron Doped Trigonal Molybdenum and Vanadium Mixed Oxides According to the Invention—Comparison with Doped Catalysts not Forming Part of the Present Invention In this example, acrylic acid has been synthetised in gas phase (using nitrogen and helium as carrier gas) starting from allyl alcohol, using Tr-MoVO or Tr-MoVFeO. Comparatively, the synthesis of acrylic acid has also been carried using doped molybdenum and vanadium catalysts not forming part of the present invention, namely Tr-MoVCuO, Tr-MoVNbO, Tr-MoVTeO, Tr-MoVTaO, Tr-MoVWO and Tr-MoVWCuO.

For each synthesis, 25 mg of catalyst have been placed between 2 layers of silicium carbide having a mean granulometry of 210 μm. The reactor was heated until the required temperature (350° C.) under an air flow of 10 mL/min and then fed with reactants (allyl alcohol/$O_2$/$H_2O$/$N_2$/He) at a

TABLE 1

| Catalyst | Temperature (° C.) | Allyl alcohol conversion (%) | Selectivity | | | | | |
|---|---|---|---|---|---|---|---|---|
| | | | Acrylic acid | Propionic acid | Acetic acid | Acrolein | Propanal | $CO_x$ |
| Tr-MoVO | 300 | 100 | 55.4 | 34.2 | 3.1 | 0.1 | 0.2 | 6.6 |
| Tr-MoVO | 350 | 100 | 61.0 | 2.5 | 12.7 | 0.9 | 0.0 | 23.7 |
| Or-MoVO | 300 | 98.9 | 46.4 | 39.6 | 2.3 | 3.5 | 3.1 | 4.6 |
| Or-MoVO | 350 | 100 | 66.3 | 10.0 | 9.0 | 0.0 | 0.0 | 14.4 |
| Te-MoVO (*) | 300 | 34.8 | 0.9 | 0.0 | 0.0 | 79.3 | 9.9 | 3.7 |
| Te-MoVO (*) | 350 | 74.7 | 10.2 | 2.0 | 0.8 | 64.1 | 14.8 | 4.7 |
| Am-MoVO (*) | 300 | 56.6 | 6.9 | 7.5 | 0.0 | 58.9 | 22.2 | 4.0 |
| Am-MoVO (*) | 350 | 99.9 | 59.0 | 9.2 | 5.1 | 14.4 | 1.6 | 10.4 |

(*) Comparative Example not forming part of the present invention

In the above table:

Allyl alcohol conversion (in %)=[(moles of allyl alcohol injected)−(moles of allyl alcohol analyzed at the outlet of the reactor)/(moles of allyl alcohol injected)]×100

Selectivity in acrylic acid (in %)=[(moles of acrylic acid analyzed at the outlet of the reactor)/ pressure of $2·10^5$ Pa. The flow rate was adjusted to 80 mL/min. The contact time of the reactants with the catalyst was of the order of 0.00031 g-cat $(mL·min^{-1})^{-1}$ and the total reaction time was 140 min. The allyl alcohol/$O_2$/$H_2O$/$N_2$+He molar ratio was set at 0.7/1.5/29.8/8 for all the experiments.

In the mixture $N_2$+He, the flow of $N_2$ was set at 6 mL/min, and the flow of He at 2 mL/min.

The results are given in the following Table 2:

TABLE 2

| Catalyst | Allyl alcohol conversion (%) | Selectivity | | | | | |
|---|---|---|---|---|---|---|---|
| | | Acrylic acid | Propionic acid | Acetic acid | Acrolein | Propanal | $CO_x$ |
| Tr-MoVO | 100 | 71.9 | 5.9 | 8.3 | 0.3 | 0.1 | 13.5 |
| Tr-MoVFeO | 100 | 78.8 | 1.1 | 8.8 | 0.7 | 0.0 | 10.2 |
| Tr-MoVCuO (*) | 100 | 68.1 | 2.6 | 11.4 | 0.0 | 0.0 | 17.7 |
| Tr-MoVNbO (*) | 100 | 67.2 | 2.9 | 10.5 | 1.0 | 0.0 | 18.3 |
| Tr-MoVTeO (*) | 20.2 | 14.5 | 9.1 | 0.0 | 58.7 | 14.1 | 3.1 |
| Tr-MoVTaO (*) | 100 | 55.2 | 4.9 | 15.4 | 0.0 | 0.0 | 24.3 |
| Tr-MoVWO (*) | 100 | 65.2 | 2.9 | 16.2 | 0.0 | 0.0 | 15.7 |
| Tr-MoVWCuO (*) | 100 | 68.1 | 2.6 | 11.4 | 0.0 | 0.0 | 17.7 |

(*) Comparative Example not forming part of the present invention

These results show that the use of trigonal iron doped molybdenum and vanadium mixed oxide leads to a better yield in acrylic acid compared with Tr-MoVO (78.8% versus 71.9%). The use of other metals such as Cu, Te, Ta or W do not have the same enhancement effect on the oxidation of allyl alcohol into acrylic acid.

The invention claimed is:

1. Process for the production of an unsaturated carboxylic acid from an alcohol in the presence of a catalyst, said process comprising one step of oxidation of an alcohol of following formula (II):

$$CH_2=C(R^1)-CH_2-OH \quad (II)$$

in which $R^1$ is a hydrogen atom or a methyl radical, to result in an unsaturated carboxylic acid of following formula (III):

$$CH_2=C(R^1)-COOH \quad (III)$$

in which $R^1$ has the same meaning as in the above formula (II), said reaction being carried out in the gas phase, the said gas phase comprising at least oxygen, and in the presence of a solid catalyst chosen from the compounds of following formula (I):

$$Mo_aVFe_bO_c \quad (I)$$

wherein:
- a, b and c denotes the atomic ratio of Mo, Fe and O respectively;
- a varies from 3 to 4 inclusive,
- b varies from 0 to 1 inclusive,
- c varies from 10 to 15 inclusive,
- said compound of formula (I) being in an orthorhombic or trigonal crystalline phase.

2. Process according to claim 1, wherein $R^1$ is a hydrogen atom and said process comprises a step of oxidation of allyl alcohol to give acrylic acid.

3. Process according to claim 1, wherein the solid catalyst is chosen among compounds of formula (I) in which a=3 and b=0 to 0.5 inclusive.

4. Process according to claim 1, wherein the solid catalyst is chosen among trigonal $Mo_3VO_c$, orthorhombic $Mo_3VO_c$ and trigonal $Mo_3VFe_{0.2}O_c$, in which c as the same meaning as in the formula (I).

5. Process according to claim 1, wherein the oxidation reaction is carried out at a temperature varying inclusively from 330 to 370° C.

6. Process according to claim 1, wherein the oxidation reaction is carried out at a temperature of 350° C.

7. Process according to claim 1, wherein the oxidation reaction is carried out at a pressure ranging from 1 to $1\cdot 10^6$ Pa.

8. Process according to claim 1, wherein within the gas phase, the alcohol of formula (II)/oxygen molar ratio varies from 0.1 to 2.

9. Process according to claim 1, wherein the oxidation reaction is carried out using a gas phase comprising nitrogen as carrier gas and in which the alcohol of formula (II)/oxygen/nitrogen molar ratio is 1/2.2/11.8.

10. Process according to claim 1, wherein the oxidation reaction is carried out using a gas phase comprising a mixture of nitrogen and helium as carrier gas and in which the alcohol of formula (II)/oxygen/nitrogen+helium ratio molar ration is 0.7/1.5/8.

11. Process according to claim 1, wherein the catalyst of formula (I) is supported by a porous solid support.

* * * * *